United States Patent [19]

Jacob

[11] Patent Number: 4,801,427
[45] Date of Patent: Jan. 31, 1989

[54] PROCESS AND APPARATUS FOR DRY STERILIZATION OF MEDICAL DEVICES AND MATERIALS

[75] Inventor: Adir Jacob, 23 Juniper La., Framingham, Mass. 01701

[73] Assignee: Adir Jacob, Framingham, Mass.

[21] Appl. No.: 19,134

[22] Filed: Feb. 25, 1987

[51] Int. Cl.⁴ .................. A61L 2/00; G01N 23/00
[52] U.S. Cl. .............................. 422/23; 422/33; 422/37; 422/21; 204/164; 250/455.1
[58] Field of Search ............... 422/21-23, 422/28, 33, 36, 37; 204/164, 298; 250/424, 455.1, 492.1

[56] References Cited

U.S. PATENT DOCUMENTS

| Re. 30,505 | 2/1981 | Jacob | 156/643 |
|---|---|---|---|
| 3,383,163 | 5/1968 | Menashi | 21/54 |
| 3,701,628 | 10/1972 | Ashman et al. | 21/54 R |
| 3,757,733 | 9/1973 | Reinberg | 118/49.5 |
| 3,851,436 | 12/1974 | Fraser et al. | 53/21 FC |
| 3,876,373 | 4/1975 | Glyptis | 422/23 |
| 3,879,597 | 4/1975 | Bersin et al. | 219/121 P |
| 3,923,568 | 12/1975 | Bersin | 156/8 |
| 3,948,601 | 4/1976 | Fraser et al. | 21/54 R |
| 3,951,709 | 4/1976 | Jacob | 156/8 |
| 3,971,684 | 7/1976 | Muto | 156/13 |
| 3,994,793 | 11/1976 | Harvilchuck et al. | 204/192 |
| 4,026,742 | 5/1977 | Fujino | 156/643 |
| 4,028,155 | 6/1977 | Jacob | 156/643 |
| 4,030,967 | 6/1977 | Ingrey et al. | 156/643 |
| 4,073,669 | 2/1978 | Heinecke et al. | 156/643 |
| 4,182,646 | 1/1980 | Zajac | 156/643 |
| 4,207,286 | 6/1980 | Gut Boucher | 422/21 |
| 4,208,241 | 6/1980 | Harshbarger et al. | 156/643 |
| 4,211,601 | 7/1980 | Mogab | 156/643 |
| 4,214,946 | 7/1980 | Forget et al. | 156/643 |
| 4,226,665 | 10/1980 | Mogab | 156/643 |
| 4,229,247 | 10/1980 | Chiu et al. | 156/643 |
| 4,255,230 | 3/1981 | Zajac | 156/643 |
| 4,256,534 | 3/1981 | Levinstein et al. | 156/643 |
| 4,264,409 | 4/1981 | Forget et al. | 156/643 |
| 4,267,013 | 5/1981 | Iida et al. | 156/643 |
| 4,298,443 | 11/1981 | Maydan | 204/192 E |
| 4,314,874 | 2/1982 | Abe et al. | 156/628 |
| 4,314,875 | 2/1982 | Flamm | 156/643 |
| 4,321,232 | 3/1982 | Bithell | 422/23 |
| 4,341,592 | 7/1982 | Shortes et al. | 156/643 |
| 4,341,616 | 7/1982 | Nagatomo et al. | 204/298 |
| 4,348,357 | 9/1982 | Bithell | 422/22 |
| 4,353,777 | 10/1982 | Jacob | 156/643 |
| 4,358,686 | 11/1982 | Kinoshita | 204/298 |
| 4,362,632 | 12/1982 | Jacob | 422/183.04 |
| 4,505,782 | 3/1985 | Jacob et al. | 156/643 |

FOREIGN PATENT DOCUMENTS 0207417 3/1986 European Pat. Off. .

*Primary Examiner*—Barry S. Richman
*Assistant Examiner*—Lyle A. Alexander
*Attorney, Agent, or Firm*—Lahive & Cockfield

[57] ABSTRACT

A process for dry sterilization of medical devices and materials in which these materials are subjected to an electrical discharge in a gaseous atmosphere to produce an active plasma to produce electrically active neutral species for surface sterilization of the devices and materials.

19 Claims, 2 Drawing Sheets

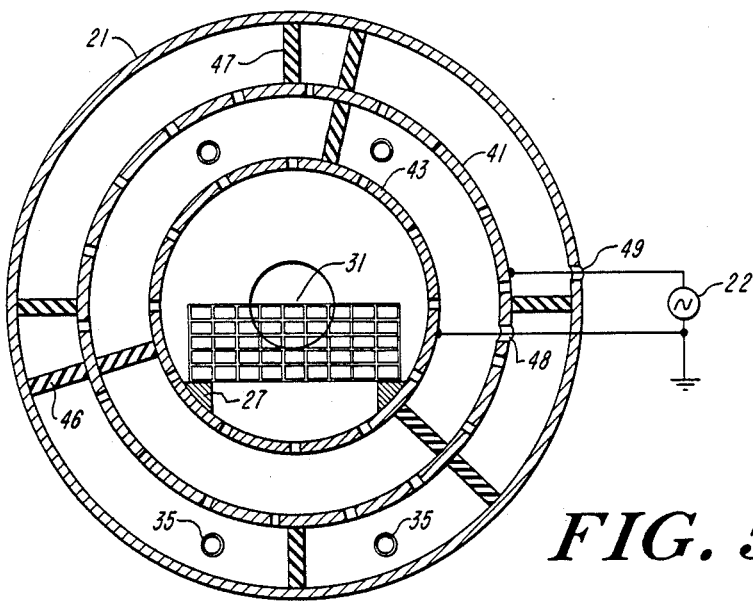
*FIG. 5*
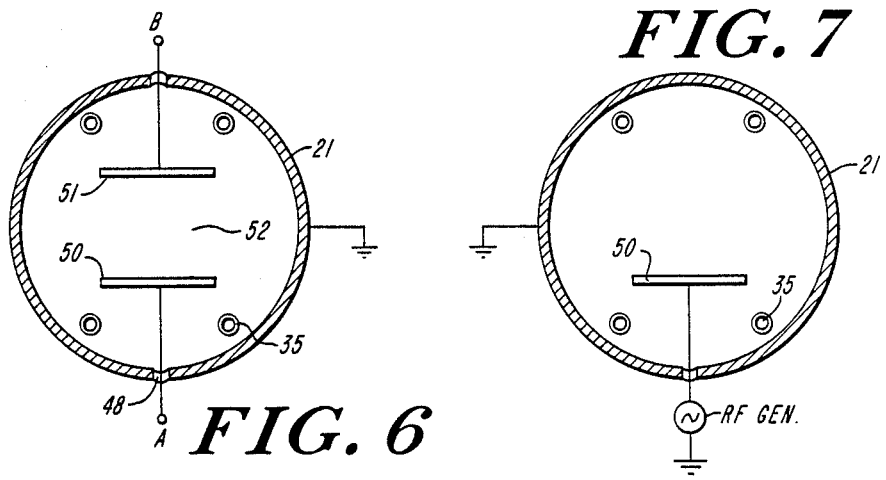
*FIG. 6*   *FIG. 7*
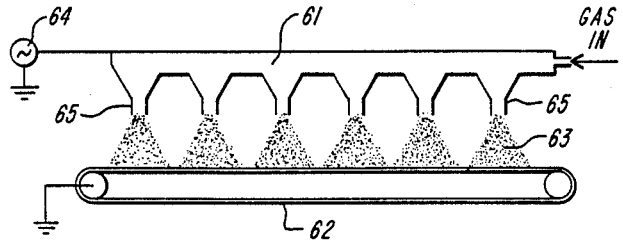
*FIG. 9*
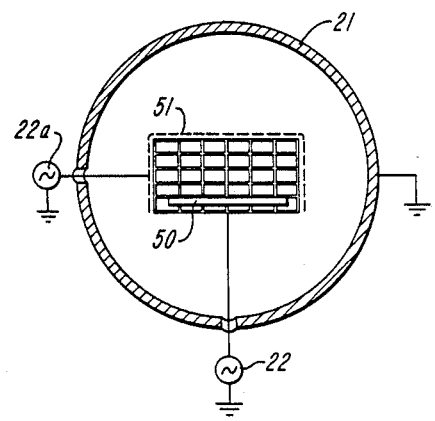
*FIG. 8*

PROCESS AND APPARATUS FOR DRY STERILIZATION OF MEDICAL DEVICES AND MATERIALS

BACKGROUND OF THE INVENTION

Modern medical practice requires the use of aseptic materials and devices, many of them meant for repeat use. In order to achieve this sterilization, processes are needed, at the manufacturer, and also at the hospitals for treatment of reusable materials and devices.

Typical of materials which are reused in the hospital environment and require repeated sterilization are major surgical instrument trays, minor surgical kits, respiratory sets, fiber optics, scopes and breast pumps.

There are a wide variety of medical devices and materials that are to be supplied from the manufacturer already packaged and sterile. Many of these devices and materials are disposable. Typical of this group are barrier packs, head coverups and gowns, gloves, sutures and catheters.

One major sterilization process in present use is that which employs ethylene oxide (EtO) gas at up to three atmospheres of pressure in a special shatter-proof sterilization chamber. This process, in order to achieve effective asepsis levels, requires exposure of the materials to the gas for at least one hour followed by a minimum of twelve hours, or longer, aeration period. The initial gas exposure time is relatively long because the sterilization is effected by alkylation of amino groups in the proteinaceous structure of any microorganism. EtO sterilization requires the attachment of the entire EtO molecule, a polyatomic structure containing seven atoms to the protein. This is accompanied by the requirement of hydrogen atom rearrangement on the protein to enable the attachment of EtO. Because of the space factors governing the attachment of such a bulky molecule, the process needs to be carried out at high pressure and be extended over a long period of time. It is, therefore, deemed very inefficient by the industry at large.

Perhaps the chief drawback to this system, however, is its dangerous toxicity. Ethylene-oxide (EtO) is a highly toxic material dangerous to humans. It was recently declared a carcinogen as well as a mutagen. It requires a very thorough aeration process following the exposure of the medical materials to the gas in order to flush away EtO residues and other toxic liquid by-products like ethylene glycol and ethylene chlorohydrin. Unfortunately, it is a characteristic of the gas and the process that EtO and its toxic by-products tend to remain on the surface of the materials being treated. Accordingly, longer and longer flush times (aerations) are required in order to lower the levels of these residues absorbed on the surface of the materials to a safe operational value. A typical volume for each batch using this EtO process is 2 to 50 cu. ft. within the health care environment.

A number of other approaches for performing sterilization have also been employed. One such process is steam autoclaving. However, this requires high temperature and is not suitable for materials which are affected by either moisture or high temperature. Another approach utilizes either x-rays or radioactive sources. The x-ray approach is difficult and expensive. The use of radioactive sources requires expensive waste disposal procedures, as well as requiring radiation safety precautions. The radiation approach also presents problems because of radiation-induced molecular changes of some materials, which, for example, may render flexible materials brittle.

It is therefore a primary object of the present invention to provide a process and apparatus for dry sterilization of medical devices and materials, which can be operated efficiently, both with respect to time and volume.

It is another object of the present invention to provide a safe, nontoxic, process for the sterilization of medical devices and materials, a process which does not employ toxic feed gases and one which does not yield toxic adsorbed surface residues.

SUMMARY OF THE INVENTION

Broadly speaking in the present invention, sterilization is achieved by exposing the medical devices and materials to a highly reducing gas plasma like that generated by gas discharging molecular hydrogen, or to a highly oxidizing gas plasma, for example, one containing oxygen. This plasma is generated by creating an electrical discharge in a gaseous atmosphere within an active zone within which the materials to be sterilized are placed.

Generation of gas plasmas is a very well developed art, which has been specifically employed in semi-conductor processing, See, for example, U.S. Pat. Nos. 3,951,709; 4,028,155; 4,353,777; 4,362,632; 4,505,782 and RE 30,505.

In one instance the gas plasma sterilization process of this invention involves evacuating a chamber to a relatively low pressure after the devices or materials to be sterilized have been placed within it. An oxidizing gaseous atmosphere is then provided to the chamber at a relatively low pressure, typically in the range 10 microns Hg to 10 torr, corresponding to a gaseous flow rate range of 20 to 1000 standard cc per minute. An electrical discharge is produced within the chamber by conventional means, such as a microwave cavity or a radio frequency (RF) excited electrode. Alternatively, RF power in the power density range 0.0125–0.05 W/cm$^3$ may be coupled into the oxidizing gas via a single electrode disposed within the chamber in a non-symmetrical electrical configuration, or via two electrodes contained within the chamber in an electrically symmetrical configuration. In either case the material to be sterilized is placed on one of the electrodes, while the chamber's wall is maintained at ground potential. The resultant discharge produces a gas plasma including both excited electrically charged gaseous species and excited electrically neutral gaseous species. For example, free radicals of atomic oxygen as well as excited molecular oxygen are formed in a discharge through molecular oxygen. These oxygen-bearing active species interact with the proteinaceous components of the microorganisms residing on the surfaces of medical devices to be sterilized, denaturing the proteinaceous molecules and achieving kill rates of microorganisms equivalent to a probability of survival of only one in a million.

The efficiency of this process is due, in part, to the fact that the active plasma entities are atomically small (usually monoatomic or diatomic) and therefore exhibit an enhanced ability to attach themselves to a proteinaceous structure and/or abstract (remove) hydrogen atoms from it. The space restriction for this type of interaction is at least one thousand times lower than that for EtO alkylation.

Several specific types of interaction take place. One specific interaction is hydrogen abstraction from amino groups. Another is rupturing ring structures, particularly those including nitrogen, or carbon-carbon bond cleavage. It is important to note that these processes produce only gaseous effluents, such as water vapor and carbon dioxide, which would not remain adsorbed on the surface of medical devices, but would be carried away from such devices with the main gas stream to the pump.

This sterilization process may be used with pre-packaged materials, such as disposable or reusable devices contained within polyethylene or another gas-permeable package. With polyethylene or Tyvek packaging, the barrier wall of the package is pervious to the relatively small active species of the sterilizing plasma, but impervious to the larger proteinaceous microorganisms. (Tyvek is a bonded polyolefin produced by DuPont). After evacuation of the chamber, and introduction of the gas or gas mixture, the gas(es) will permeate the package wall with a dynamic free exchange of gas(es) from within and from outside the package. Upon striking a microwave or an RF discharge to form the plasma, and, depending upon electrical configuration, the discharge may either be formed throughout the volume of the chamber, so that plasma is actually also created within the package or, alternatively, the package may be placed in an electrically shielded (field-free) glowless zone so that it is subject to predominantly electrically neutral active species which pass through the packaging wall to interact with the surface of the materials it contains.

In yet a different electrical configuration, the packages containing devices to be sterilized can be placed on a conveyor belt and swept into an atmospheric pressure corona discharge gap operated in ambient air. With this configuration, the discharge electrodes are comprised of a grounded conveyor belt forming the bottom electrode, while the top electrode is comprised of a metal block with multiple needle-like nozzles for the dispersion of gas. Sterilization with this continuous, in-line, apparatus, is brought about by ozone formation, due to presence of discharged oxygen in air, or due to any other oxidizing gas mixture that can be introduced into the discharge gap via a through plurality of nozzles, which are an integral part of the top electrode. This corona discharge will normally operate in the power density range 5–15 W/cm$^2$ in the frequency range 10–100 KHz and 13–27 MHz, associated with gas flows in the range of several standard liters per second.

In order to enable device sterilization by a strongly oxidizing plasma when employing the process with for example polyethylene packaging, it is necessary to provide that oxygen-bearing active species can permeate through a typical organic package barrier (like that of a polyethylene plastic pouch) in the first place, and that a sufficient number of these species traverse that barrier in order to effectively kill all microorganisms on a medical device enclosed within the pouch. Relevant oxidizing species can be obtained by plasma discharging diatomic gases like oxygen, nitrogen, halogens, or inary mixtures of oxygen and hydrogen, oxygen and nitrogen, oxygen and inert gases, or the gaseous combination of oxygen, nitrogen and inert gases like helium or argon. The predominance of oxygen in the above mixtures is preferred but not mandatory. A predominance of nitrogen, for example, will result in higher process temperatures during sterilization for a given reaction pressure and power density. The inert gas fraction can be variable in the range 10 to 95%; the higher the fraction, the lower the processing temperature for a given pressure and power density. However, sterilization exposure time increases the higher the inert gas fraction in the mix. Substitution of argon for helium, for example, will result in higher sterilization temperatures for a given pressure and power density. In this case, instability of the gas discharge operation may set in, requiring a power density increase at a given pressure, compared to that employed with helium, resulting in higher process temperatures.

Effective sterilization can also be obtained with a pure reducing hydrogen plasma due to its very strong hydrogen atom abstraction (removal) capabilities from proteinaceous structures of microorganisms. Hydrogen in its mixtures with either nitrogen or oxygen, or with both, in the presence or absence of an inert gas, will show effective sterilization capabilities over a wide range of concentrations in these mixtures.

The first objective of facilitating the gaseous permeation through an organic barrier is accomplished by evacuating the chamber (containing the loaded pouches) to a base pressure of approximately 20 microns Hg. This rids the pouches of previously entrapped atmospheric air, and equalizes the pressure inside the pouch to that inside the chamber (across the organic barrier). The subsequent introduction into the chamber of an oxygen-containing gas, in a typical situation, will establish an instantaneous higher pressure inside the chamber (outside the pouch) relative to that inside the pouch. This pressure gradient across the pouches' barrier will serve as the initial driving force of gas into the pouch. At an equilibrated state, an active and ongoing interchange of molecules across the barrier will take place, at all times attempting to maintain the same pressure on both sides of the organic barrier. Upon striking a discharge through this gas, oxygen-bearing active species will be generated. Typically these active species will be deactivated in large amounts by the organic barrier. This will commonly substantially reduce the availability of these active species to do the sterilizing job.

Therefore, in order to accomplish the second objective of generating a sufficient number of oxidizing species traversing the organic barrier of a package, the organic barrier must be passivated in such a way as to substantially reduce its take-up of oxygen-bearing active species needed as a sterilizing agent and which must render a final non-toxic medical device, without the formation of any toxic by-products.

One such passivation method consists of simultaneously introducing into the chamber a gaseous mixture, which in addition to oxygen-containing gas(es), also contains selected other gases as set forth below:

1. Organohalogens, based on carbon and/or silicon, attached to any of the known halogens. particularly those organic compounds of carbon and/or silicon that are saturated or unsaturated and contain in their molecular structures one (1) or two (2) carbon or silicon atoms attached to: a predominance of fluorine atoms; a predominance of chlorine atoms; a predominance of bromine or iodine atoms; an equal number of fluorine and chlorine atoms simultaneously; an equal number of chlorine and bromine atoms simultaneously; an equal number of fluorine and bromine atoms simultaneously; an equal number of fluorine and iodine atoms simultaneously; an equal number of chlorine and iodine atoms simultaneously. A predominance of fluorine in these compounds includes structures where all other atoms attached to a carbon or a silicon atom can be all the other halogens, or only one or two other halogens out of the four halogens known, in conjunction with other atoms, as for example hydrogen. The same comments apply to a predominance of chlorine, bromine and iodine. For the latter, however, the simultaneous presence of bromine is unlikely to be practical due to a low volatility of the structure, but the simultaneous presence of fluorine or chlorine, or both, is practical. It is worth noting that hydrogen-containing organohalogens will have a tendency to polymerize under plasma conditions, and in some cases, be flammable in as-received condition.

Most effective sterilizing mixtures of oxygen and an organohalogen are those where the organohalogen is a mixture of organohalogens in itself, either based on carbon and/or silicon, where the oxygen fraction is over 70% by volume; yet sterilization will be effected for lower oxygen content at the expense of excessive halogenation of the surface of the material to be sterilized, and at the expense of excessive loss of transparency of the wrapping pouch.

2. Organohalogens in conjunction with either nitrogen or an inert gas like helium or argon. In these cases, it is considered practical to keep the fraction of the inert gas in predominance in order to keep the process temperature as low as possible. Inert gas fractions up to 95% by volume will be effective in killing microorganisms. The nitrogen fraction is ideally kept below that of the oxygen fraction.

3. Inorganic halogens, defined as compounds not containing carbon or silicon, but preferably containing as the central atom or atoms either hydrogen, nitrogen, sulfur, boron, or phosphorus linked to any of the known halogens in a similar manner as described for the organohalogens under item 1 above, or defined as compounds that contain only halogens without a different central atom, like for example molecular halogens (e.g., $F_2$, $Cl_2$) and the interhalogens which contain two dissimilar halogen atoms (e.g., Cl-F, I-F, Br-Cl based compounds, etc.). Also in this case the inorganic halogen maybe, in itself, a mixture of different inorganic halogens as defined above.

Most effective sterilizing mixtures of oxygen and an inorganic halogen are those where the oxygen fraction is over 80% by volume; yet sterilization will be effected for lower oxygen content at the expense of excessive halogenation of the surface of the material to be sterilized, and at the expense of excessive loss of transparency of the wrapping pouch.

4. Inorganic halogens in conjunction with either nitrogen or an inert gas as described in item 2 above.

5. Inorganic oxyhalogenated compounds, not containing carbon or silicon, but preferably contain either nitrogen, phosphorus, or sulfur, each of which is simultaneously attached to oxygen and a halogen (e.g., NOCl, $SOCl_2$, $POCl_3$, etc.). More specifically, the nitrogen-oxygen, or the sulfur-oxygen, or the phosphorus-oxygen entities in the previous examples are linked to any of the known halogens in a similar manner as described for the organohalogens under item 1 above. The inorganic oxyhalogenated fraction may be, in itself, a mixture of different inorganic oxyhalogenated compounds as defined above.

Most effective sterilizing mixtures of oxygen and an inorganic oxyhalogenated structure are those where the oxygen fraction is over 70% by volume; yet effective sterilization will be obtained for lower oxygen content at the expense of excessive halogenation of the surface to be sterilized, and at the expense of excessive loss of transparency of the wrapping pouch.

6. Inorganic oxyhalogenated compounds in conjunction with free nitrogen or an inert gas as described in item 2 above.

7. Multicomponent mixtures comprised of members in each of the aforementioned groups. The simultaneous presence of free nitrogen and an inert gas like helium or argon in any of the above mentioned groups, or in multicomponent mixtures comprised of members in each of the aforementioned groups, will also be effective in killing microorganisms. The free nitrogen fraction should be ideally below that of oxygen in order to maintain a lower reaction temperature.

More specific and relatively simple multicomponent mixtures that are effective sterilants as well as effective organic barrier passivation agents are listed below:

Specific Multicomoonent Mixtures Comprised of Fractions A+B (percent of fraction is by volume)

| Fraction A | Fraction B |
|---|---|
| $O_2$(92-97%) | $CF_4$(3-8%) |
| [$O_2$(40%)—He(60%)] | $CF_4$(0.25-3%) |
| [$O_2$(8%)—$CF_4$(92%)] | He(80%) |
| [$O_2$(17%)—$CF_4$(83%)] | He(80%) |
| [$O_2$(83%)—$CF_4$(17%)] | He(80%) |
| [$O_2$(92%)—$CF_4$(8%)] | He(80%) |

Many of the aforementioned gas mixtures are, in themselves, novel chemical compositions.

The plasma discharge through such a composite mixture will, for example, create both oxygen-bearing and fluorine, or chlorine-bearing active species simultaneously. The latter will predominantly be responsible for passivating the organic barrier, since fluorination or chlorination, rather than oxidation of the organic barrier is favored thermodynamically. Therefore, the take-up of fluorine or chlorine-bearing active species by the organic barrier of the pouch will be preferential. This will leave a relatively larger fraction of oxygen-bearing active species available for sterilization, since the latter cannot easily be taken up by a fluorinated or chlorinated surface.

In addition, sterilization by oxygen-bearing active species is aided, for example, by simultaneously discharging an oxygen-containing and fluorine or chlorine containing gas residing inside the enclosing pouch. This gas had previously permeated through the organic barrier prior to the commencement of the discharge. The plasma, which is generated within the pouch, much in the same way as previously described for the plasma generated within the chamber, will create active species that contain both oxygen and fluorine or chlorine within the pouch directly. As previously described, the competition for take-up by the organic barrier (pouch) will be won by the fluorinating or chlorinating species, leaving a larger net concentration of active species containing oxygen to do an effective sterilizing job.

However, residual fluorine or chlorine-bearing active species within the pouch and not taken-up by it will also perform effective sterilization, since they are strongly chemically oxidizng agents. But, the fraction of fluorine or chlorine-containing gas in the original composite gaseous mixture, is substantially smaller than the oxygen-containing component. Thus, a major portion of microorganisms kill will be attributed to the oxygen-bearing species in the plasma. In either case, however, the end result is a continuous attack on the proteinaceous structure of the microorganism resulting in its degradation and fragmentation into gaseous products. This chemical action by the reactive plasma is to initially modify (denature) the proteinaceous network of the microorganism, disrupting its metabolism at a minimum, but more commonly impeding its reproduction.

DESCRIPTION OF THE DRAWINGS

In the drawing

FIGS. 5, 6, 7, 8 and 9 are cross sectional views of alternative embodiments.

DESCRIPTION OF PREFERRED EMBODIMENTS

Figure 1:
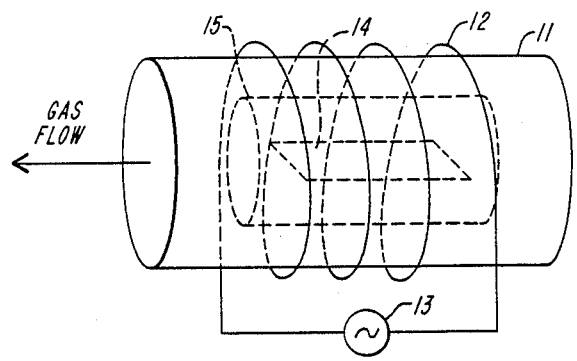
FIG. 1 is a general diagrammatic illustration of an apparatus suitable for use in the practice of this invention.

FIG. 1 is a general diagrammatic illustration of an RF excited discharge chamber of the type used in the process of this invention. The cylindrical chamber 11 is formed, in this instance, of glass or quartz and encloses within it the material 14 to be treated. The chamber is commonly connected to a mechanical vacuum pump (not shown) that establishes sub-atmospheric pressure conditions within the chamber. An exciter coil 12 couples RF energy from RF source 13 to the gas enclosed within the gas tight chamber creating a plasma therein.

Alternatively, a microwave discharge cavity operating at 2450 MHz may replace the RF exciter coil to couple power into the gas. With a suitable selection of a reducing gas, like hydrogen, or an oxidizing gas, such as oxygen, as a typical example, a discharge may be initiated and maintained within the chamber. In the gas plasma formed by that discharge a number of excited species, both molecular and atomic, are formed. The interaction of these species with a surface of the device or material to be sterilized accomplishes the sterilization in the manner described above. The time duration of the process needed to achieve satisfactory sterilization will vary with other parameters of the discharge such as gas flow, pressure, RF power density, and load size.

In one physical embodiment the apparatus may include an inner perforated metallic cylinder mounted generally concentric with the long axis of the chamber to form within the perforated cylinder a glowless, field-free zone. In FIG. 1 a perforated cylindrical shield 15 of this type is shown in dotted lines.

Figure 2:
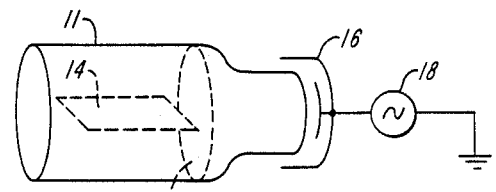
FIG. 2 is a cross-sectional view of a sterilization chamber for use in the practice of the invention.

When, as illustrated in FIG. 2, a microwave energy source 18 at 2540 MHz. is employed in lieu of the RF generator 13, the perforated metallic cylinder cannot be mounted concentric about the long axis of the chamber. Instead, the miCrowave cavity 16 is mounted at one end of chamber 11, and a perforated metallic shield 17 may be placed just beyond it toward the opposite end of the chamber spanning the entire diameter cross section of the chamber, thus creating a field-free and glowless reactive zone immediately below it and away from the microwave cavity. These arrangements permit material 14 placed within this zone to be generally isolated from electrically charged species, while allowing the electrically neutral reactive plasma species, such as oxygen radicals, to interact with the surface of the material to be sterilized. In this manner, sterilization is commonly effected at lower process temperatures.

In the most preferred embodiments the chamber is formed of a metal outer shell with either a single internal perforated cylindrical shield, or perhaps with two such metallic shields, the RF energy being coupled, in this latter configuration between the two conducting perforated cylinders. In either case, the discharge glow is confined to the space between the inner wall of the chamber and the surface(s) of the perforated cylinder(s), leaving the work volume defined by the inner perforated cylinder field-free, void of the plasma glow, and at a relatively low operating temperature. With a microwave cavity replacing the RF energy source, a single metallic perforated shield can be used and placed just below the cavity in accordance with the operational description given for FIG. 2.

Figure 3:
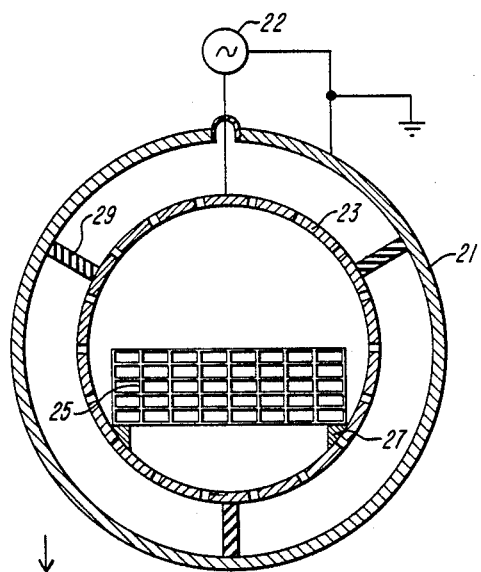
FIG. 3 is a cross-sectional view of another embodiment of a sterilizaton chamber for use in the practice of the invention.
Figure 4:
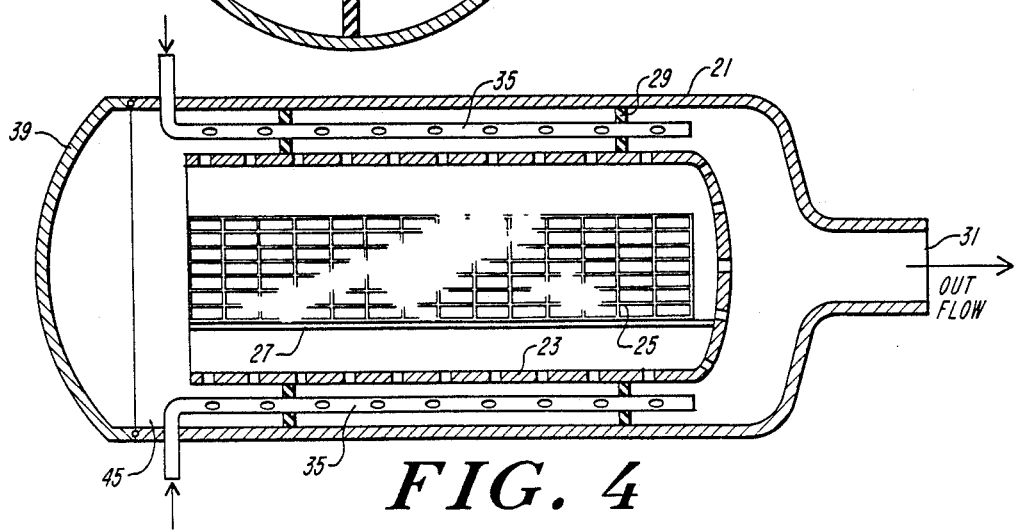
FIG. 4 is a side view of the apparatus of FIG. 3.

One such chamber configuration is illustrated in FIGS. 3 and 4. The cylindrical outer wall 21, typically formed of aluminum or stainless steel is maintained at ground potential, serves as the chamber enclosure. Suitable dimensions for this chamber are a diameter of 36" and a length of 48". A metallic perforated inner cylinder 23 is mounted on insulating spacers 29 within the chamber so that it is oositioned generally parallel with the long axis of the outer wall 21 of the chamber. These spacers may be formed of any suitable non-reactive and insulating type of material such as ceramic. The cylinder perforations are typically 2.5 mm diameter holes spaced in all directions from one another by approximately 0.5 cm in a triangulated manner. Longitudinal support rails 27 are fastened to the inner wall of the perforated cylinder 23 to support a wire basket 25 in which the materials and devices to be sterilized are placed. A suitable RF source 22 is coupled between the grounded outer chamber wall 21 and the perforated inner cylinder 23. Usually this RF source should be capable of producing an RF output in the range 0.0125 to 0.05 W/cm$^3$ at frequencies in the 10–100 kilohertz or 13–27 megahertz range.

As illustrated in FIG. 4, an evacuation port 31 at the end of cylinder 21 is connected to a pump (not shown) and provides for suitable evacuation of the chamber. The gas supplied for the discharge is generally flowed through the chamber by means of perforated diffusion tubes 35. Alternately, gas may be introduced into the chamber via a gas dispersion device (not shown) mounted behind chamber door 39 from the inside.

Material to be sterilized may be placed within wire basket 25 resting on rail 27 through the entry port behind chamber door 39. Chamber door 39 may be any suitable closure that can be conveniently opened and closed and left in a sealed position during evacuation and the gas discharge operation.

FIG. 5 illustrates a second preferred embodiment of the apparatus for practicing the process of the invention. In this configuration, the outer chamber wall 21 is again formed of metal, such as aluminum or stainless steel and is electrically grounded and of similar dimensions to that illustrated in FIG. 3. Mounted within the chamber is an inner concentric cylinder 43 formed of a perforated metal and supported on insulating support struts 46. The spacing between the inner wall of the chamber and the perforated interior cylinder may range typically from 10 to 17 cm where the chamber has an I.D. of 36". A second metallic perforated cylinder 41 is concentrically mounted intermediate between the inner perforated cylinder 43 and the inner wall of the chamber. This second perforated cylinder is supported on insulating struts 47 and is spaced typically 4 to 7 cm away from the inner perforated cylinder 43. The insulator struts may again be formed of a ceramic material. Mounted on the interior of the inner concentric cylinder 43 are support rails 27 for carrying a wire basket which would contain the materials to be sterilized. Both the outer chamber wall 21 and the inner perforated cylinder 43 are electrically connected to point of potential reference (ground). Electrical connections would most usually be made through ceramic seal feedthroughs 48 and 49. The intermediate cylinder 41 is electrically connected to one side of the RF power supply 22, the other side of which is connected to the point of potential reference.

While a variety of conventional RF sources may be used, the most typical value for the RF frequency is 13.56 MHz or, alternatively, 10–100 KHz. As in the embodiment of FIG. 4 longitudinally extending gas diffusion tubes 35 may be employed to provide the gas to the interior of the chamber. Typically each tube would have holes of diameter between 0.5 and 1.5 mm, spaced approximately 1" apart along its length. The hole diameters closer to the gas source would be of the smaller diameter. Alternatively, gas inlets may be provided behind door 39. As indicated in embodiments of FIGS. 3, 4 and 5 the perforated inner cylinders may be open-ended at both ends or, may be closed with the same perforated stock as is used to form the cylinder(s). The sterilization chambers described in FIGS. 3, 4 and 5 may be connected to a microwave discharge source, typically operating at 2540 MHz, in lieu of an RF energy source. In this case, the concentric perforated metallic cylinder(s) may be replaced by a single perforated shield in accordance with the operational description given for FIG. 2.

FIG. 6 illustrates a third preferred embodiment of the apparatus for practicing the process of the invention. In this diagrammatic description the outer chamber wall 21 is again formed of metal, such as aluminum or stainless steel, and is of similar dimensions to that illustrated in FIG. 3. Mounted within the chamber are two planar, metallic, electrodes 50 and 51, preferably constructed of aluminum which may be coated with insulating aluminum oxide. The gap 52 between the electrodes, 50 and 51, is adjustable by virtue of the movable bottom electrode 50. Terminals A and B are connected to the electrodes via an insulating feedthrough 48. The outer end of these terminals may be connected to an RF source (not shown) in such a way that when terminal B is connected to a ground potential, terminal A must be connected to the RF source, or vice versa, providing for an electrical symmetrical configuration. The work load to be sterilized is placed on bottom electrode 50.

It is important to maintain the distance between the electrodes always smaller than the distance of the RF-powered electrode's edge to the grounded chamber's wall. This enables a well defined and intense plasma glow to be confined to space 52 between the electrodes and prevents deleterious sparking. The electrode material may also be made of the perforated stock previously mentioned. However, it is desirable to have the RF-powered electrode made of solid stock to enable water-cooling of that electrode. The bottom electrode may also be made of solid stock to enable a cool surface upon which the work load to be sterilized will be placed. This chamber will commonly be evacuated to 10 microns Hg before gas introduction via the perforated gas diffusion tubes 35. Practical device sterilization can be obtained with process parameters for gas flow rates in the range 20 to 1000 scc/m, corresponding to a total sterilization reaction pressure of 10–1000 microns Hg, at a range of RF power densities of 0.0125 to 0.05 W/cm$^3$.

FIG. 7 illustrates in diagrammatic form yet another preferred embodiment for practicing the process of the invention. The outer wall of chamber 21 is again formed of metal, such as aluminum or stainless steel maintained at ground potential, and is of similar dimensions to that illustrated in FIG. 3. Mounted within the chamber is a single planar, metallic, electrode 50, preferably constructed of aluminum which may be coated with insulating aluminum oxide to reduce RF sputtering. This electrode is commonly connected to an RF source in the MHz range and carries the work load to be sterilized. This electrode has commonly a total surface area which is at least four times smaller than the total internal surface area of the chamber.

This electrical configuration is usually referred to as asymmetric and is conducive to generating an extremely uniform plasma glow filling the entire volume of the process chamber. It is also responsible for the development of a characteristic accelerating potential at the surface of electrode 50, associated with a thin "dark space" through which positive plasma ions will accelerate and impinge on the electrode and the work load it normally carries.

The main advantage of this configuration is its ability to render efficient sterilization at relatively low power densities in the range of 0.0125–0.025 W/cm$^3$. This configuration is also easily scalable as a function of work load size and its configuration.

This process chamber commonly operates with at least an order of magnitude lower pressure than the pressure for chambers described in FIGS. 1 through 6, while the gas dispersion tubes 35 are similar in construction to those previously mentioned. To prevent RF sputtering of electrode 50 due to positive ion bombardment, it may either be hard-anodized or alternatively aluminum oxide spray-coated.

One particular sub-configuration to that described in FIG. 7 is illustrated in FIG. 8. In this configuration a metallic perforated enclosure 51 totally surrounding and containing electrode 50 may be used, and connected to a separate RF source 22a. This perforated enclosure may be equipped with an open/close hinging mechanism (not shown) to enable access for material to be sterilized to be placed on electrode 50 contained within enclosure 51. This yields the beneficial effect of being able to separately control the abundance of sterilizing active species and their impinging energy. RF power applied to electrode 50, which may or may not include a negative DC potential from a separate DC supply, (not shown), will control energy of ion impingement, while RF power applied to the auxiliary perforated enclosure will control active species abundance.

With this configuration, RF power sources operating at 100 KHz and 13.56 MHz may be used in the various posssible permutations. Interesting results are obtained by mixing both frequencies while being applied to a single element. Commonly, one frequency has to be applied at a higher power fraction, usually around 90% of the total applied power to the same element. Such interesting process results were obtained when the two different frequencies were mixed and applied to electrode 50 in the absence of any auxiliary perforated enclosure. The mixed frequency concept also lends itself to low power density sterilization in the range 0.0125 to 0.025 W/cm$^3$, with the advantage of maintaining the overall temperature relatively low (below 50° C.), particularly when electrode 50 is water-cooled.

It is worth noting that the auxiliary perforated enclosure ought to be of high mesh transparency to allow the plasma glow to extend past it and contact electrode 50. Best operating conditions will be obtained for the smallest surface area of this perforated metallic enclosure.

FIG. 9 illustrates diagrammatically a preferred embodiment for practicing the process of the invention under atmospheric pressure conditions in ambient air. In this configuration no vacuum capability is required. Material to be sterilized is placed on grounded conveyor belt 62 which sweeps the load across the discharge gap created between conveyor belt 62 and RF-powered electrode 61. The powered electrode produces of a large plurality of needle-like discharges electrets 65, which create individual discharge sparks toward the counter grounded electrode 62. The larger the gap between the electrodes, the higher the power needed to initiate the discharge in air.

Sterilization is effected due to ozone formation following the discharge of oxygen in the ambient air. Power density requirements in the range 5 to 15 W/cm$^2$ are not uncommon. Maintaining a controlled relative humidity of 50 to 60% in the discharge gap will facilitate initiation of the discharge and promote atomic oxygen generation. The latter serves as a precursor to ozone formation, the final desired sterilant in this configuration.

Ozone toxicity inhibits wide acceptance of such a corona discharge in air for the purpose of medical device sterilization. Alternatively, therefore, the RF-powered electrode 61 may assume a configuration comprised of multiple open nozzles 65, capable of dispersing oxidizing gases immediately adjacent to conveyor belt 62. In this configuration the discharge would still be created in ambient air, however the dispersion through the open nozzles 65 of a judiciously selected feed gas will increase the local concentration of its active species 63 relative to that of ozone. In this manner, sterilization would be attributable to active species derived from any feed gas introduced into the hollow RF-powered electrode 61 and not to the deleterious ozone gas.

The dispersing nozzles 65 may assume different configurations. For example, separate nozzle tubes may be inserted into a hollow section of electrode block 61, which may or may not be of different material than electrode block 61. These 61 tubes may also be screwed into electrode block for easy replacement. A typical hole size for each individual nozzle is in the range 0.015–0.040".

The advantages of this discharge configuration are mainly in terms of system simplicity and in the context of continuous operation, coupled with the ability to easily change the residence time of a work load within the discharge gap.

Disadvantages are commonly associated with erosion and degradation of both electrode block 61 and conveyor belt 62. Electrode 61 should be constructed from oxidation-resistant materials (e.g., tungsten, moly bdenum or alloys thereof). The grounded conveyor belt 62 ought to be resistant to electrical punch-through and be constructed from fluorinated, or fluorinated/chlorinated hydrocarbons (e.g., DuPont products). High melting polyimides or Kalrez-like synthetics may serve as alternate construction materials for the conveyor belt. Kalrez is a polyimide manufactured by DuPont.

Set forth below are specific examples of suitable operating parameters for effective sterilization employing an apparatus as illustrated in FIG. 1 where the outer chamber wall is formed of quartz glass. These results were achieved with a chamber 8" ID. by 8" long. In some examples operation included the metallic perforated cylinders as indicated in the embodiments of FIG. 3 and 4 to provide device sterilization in a field-free and glow-less operation. In others the configuration was without such shielding internal cylinders.

For each of the examples the general technique involved was one in which the material to be sterilized was placed within a Tyvek bag which itself was sealed and placed in a wire basket within the chamber.

The materials used for verification of sterilization effectiveness were "Attest" vials obtained from 3M Company, each vial contained a bacterial strip having an original spore population of not less than $\times 10^6$ Bacillus Subtilis var Niger per strip. The strips contained in the permeable plastic vials were not brought into contact with the culture solution contained in any of the vials. The vials prior to sterilization were placed within the Tyvek bags during the plasma sterilization.

For each example the chamber was first evacuated to an initial low pressure level after the materials (in the bags or pouches) were placed within the wire basket in the chamber. The chamber was thereafter filled with the appropriate gas prior to striking the discharge, and the gas continued to flow through the chamber at a controlled rate to establish a steady state sterilization pressure. The discharge was initiated by the application of RF power as indicated. The discharge was maintained for a controlled time period at the end of which the chamber was first evacuated, then backfilled with air and later opened and the samples removed. The temperature within the chamber during the process was maintained at less than 60° C.

Subsequent to the tests the spore strips were submitted to an independent testing laboratory which performed a total plate count on the sample strips using a procedure in which 100 milliliters of sterile deionized water were added to each strip in a sterile whirl-pak bag. The bag was then placed in a lab blender for 10 minutes. One 10 milliliter aliquot of sample, a duplicate one milliliter sample, and two consecutive $10^{-1}$ dilutions were plated using Tryptic Soy Agar. The plates were then incubated at 30°–35° C. for 72 hours. After incubation, the plates were read and recorded, and the results calculated on a Colony Forming Unit (CFU) basis.

EXAMPLE 1

| (Without internal shield cylinder) | |
| --- | --- |
| Gas: | O$_2$ (Pure) |
| Flowrate: | 24 scc/min |
| Pressure: | 0.3 torr |
| Power Density: | 0.045 W/cm$^3$ |
| Exposure time: | 30 min. |
| Resultant microbial count: | <10 CFU (below sensitivity limit of counting technique) |
| Percent kill: | 99.9999% |

EXAMPLE 2

| (Without internal shield cylinder) | |
| --- | --- |
| Gas: | O$_2$ (Pure) |
| Flowrate: | 125 scc/min |
| Pressure: | 0.8 torr |
| Power Density: | 0.03 W/cm$^3$ |
| Exposure time: | 30 min. |
| Resultant microbial count: | <10 CFU (below the sensitivity limit of counting technique) |
| Percent kill: | 99.9999% |

EXAMPLE 3

| (Without internal shield cylinder) | |
| --- | --- |
| Gas: | O$_2$/CF$_4$ (8%) |
| Flowrate: | 32 scc/min |
| Pressure: | 0.3 torr |
| Power Density: | 0.027 W/cm$^3$ |
| Exposure time: | 30 min. |
| Resultant microbial count: | <10 CFU (below the sensitivity limit of counting technique) |
| Percent kill: | 99.9999% |

EXAMPLE 4

| Field-Free Operation (Employing Shielding Perforated Cylinder) | |
| --- | --- |
| Gas: | O$_2$/CF$_4$ (8%) |
| Flowrate: | 32 scc/min |
| Pressure: | 0.3 torr |
| Power Density: | 0.027 W/cm$^3$ |
| Exposure time: | 30 min. |
| Resultant microbial count: | <20 CFU (at the sensitivity limit of counting technique) |
| (Percent kill: | 99.9999% |

EXAMPLE 5

| (Without internal shield cylinder) | |
| --- | --- |
| Gas: | He(59.85%)—O$_2$(39.90%)—CF$_4$(0.25%) |
| Flowrate: | 45 scc/min |
| Pressure: | 0.35 torr |
| Power Density: | 0.030 W/cm$^3$ |
| Exposure time: | 30 min. |
| Resultant microbial count: | <10 CFU |
| Percent kill: | 99.9999% |

EXAMPLE 6

| (Without internal shield cylinder) | |
| --- | --- |
| Gas: | He(59.85%)—O$_2$(39.90%)—CF$_4$(0.25%) |
| Flowrate: | 44 scc/min |
| Pressure: | 0.35 torr |
| Power Density: | 0.019 W/cm$^3$ |
| Exposure time: | 60 min. |
| Resultant microbial count: | <10 CFU |
| Percent kill: | 99.9999% |

EXAMPLE 7

| (Without internal shield cylinder) | |
| --- | --- |
| Gas: | O$_2$(60%)—He(40%) |
| Flowrate: | (total) 47 scc/min |
| Pressure: | 0.35 torr |
| Power Density: | 0.030 W/cm$^3$ |
| Exposure time: | 30 min. |
| Resultant microbial count: | <10 CFU |
| Percent kill: | 99.9999% |

EXAMPLE 8

| (Without internal shield cylinder) | |
| --- | --- |
| Gas: | O$_2$ (pure) |
| Flowrate: | 25 scc/min |
| Pressure: | 0.3 torr |
| Power Density: | 0.015 W/cm$^3$ |
| Exposure time: | 55 min. |
| Resultant microbial count: | <10 CFU |
| Percent kill: | 99.9999% |

EXAMPLE 9

| Field-Free Operation (Employing Shielding Perforated Cylinder) | |
| --- | --- |
| Gas: | O$_2$ (pure) |
| Flowrate: | 49 scc/min |
| Pressure: | 0.45 torr |
| Power Density: | 0.038 W/cm$^3$ |
| Exposure time: | 60 min. |
| Resultant microbial count: | <10 CFU |
| Percent kill: | 99.9999% |

Having described the specific process and apparatus of the invention as defined by the below appended claims.

1. A method for sterilization of medical devices and material comprising the steps of, placing said devices and materials within a metallic perforated electrode, generally cylindrical in shape, said electrode being positioned within, and generally concentric with, a gas-tight confining chamber, said chamber being generally cylindrical, formed from metal and connected to a point of potential reference, evacuating said chamber to a substantially low pressure and introducing a gas into said chamber, initiating an electrical discharge in said gas within said chamber by application of RF voltage between said internal perforated electrode and the metal chamber wall, creating a gas plasma, having a substantially field free and glowless volume within the perforated electrode containing said devices and materials, whereby said devices and material are contacted by substantially electrically neutral active species at a temperature below that which would be detrimental to said devices and materials, maintaining said gas plasma for a controlled period of time, maintaining a flow of said gas through said chamber while maintaining a pressure within the range of 10 microns Hg to 10 torr during said electrical discharge; and evacuating the gas plasma residual gases from said chamber prior to withdrawing said devices and materials from it.

2. A method for sterilization of medical devices and materials enclosed within sealed pouches formed of gas permeable materials comprising the steps of:

placing said pouches containing said materials or devices to be sterilized within a metallic perforated electrode generally cylindrical in shape, said electrode positioned within, and generally concentric with a gas-tight confining chamber, said chamber being generally cylindrical, formed from metal and connected to a point of potential reference, evacuating said chamber to a substantially low pressure and introducing a gas into said chamber, initiating an electrical discharge in said gas within said chamber by application of RF voltage between said internal perforated electrode and the metal chamber wall creating a gas plasma, and having a substantially field free and glowless volume within the perforated electrode containing said pouches, said pouches containing said medical devices and materials, whereby said devices and materials are contacted by substantially electrically neutral active species at a temperature below that which would be detrimental to said device and materials, maintaining said gas plasma for a controlled period of time, maintained a flow of said gas through said chamber while maintaining a pressure with the range of 10 microns Hg to 10 torr during said electrical discharge; and evacuating the gas plasma residual gases from said chamber prior to withdrawing said sealed pouches from it.

3. A method for sterilizing medical devices and materials enclosed within pouches formed of gas permeable materials comprising the steps of, placing said pouches containing said devices and materials within a first metallic perforated electrode generally cylindrical in shape, said electrode being positioned within and generally concentric with a gas-tight confining chamber, said gas-tight chamber being metallic and generally cylindrical, said gas-tight chamber and said first perforated electrode being connected to a point of potential reference, said chamber enclosing a second perforated metallic electrode positioned between and generally concentric with said gas-tight chamber and said first perforated electrode, evacuating said chamber to a substantially low pressure and introducing a gas into said chamber, initiating an electrical discharge in said gas within said chamber by application of RF voltage between said second perforated electrode and said point of potential reference creating a gas plasma having a substantially field free and glowless volume within said first perforated electrode containing said devices and materials, whereby said devices and materials are contacted by substantially electrically neutral active species at a temperature below that which would be detriental to said devices and materials, maintaining said gas plasma for a controlled period of time, maintaining a flow of said gas through said chamber while maintaining a pressure within the range of 10 microns Hg to 10 torr during said electrical discharge; and evacuating the gas plasma residual gases from said chamber prior to withdrawing said pouches from it.

4. A method in accordance with claim 1, 2 or 3 wherein said gas is an oxidizing gas.

5. A method in accordance with claim 1, 2 or 3 wherein said gas is a reduuoing gas.

6. A method in accordance with claim 1, 2 or 3 wherein said gas is substantially pure oxygen.

7. A method in accordance with claim 1, 2 or 3 wherein said gas is a gaseous mixture of oxygen and $CF_4$.

8. A method in accordance with claim 1, 2 or 3 wherein said gas is a mixture of 80% oxygen, 20% $CF_4$.

9. A method in accordance with claim 1 and further including a second perforated metallic cylinder positioned between said chamber wall and said first perforated metallic cylinder, said first perforated cylinder and said chamber wall being electrically connected together to a point of potential reference, said RF voltage being applied between said second perforated metallic cylinder and said point of potential reference.

10. A process in accordance with either of claims 1, 2 or 3 wherein said gas atmosphere comprises one or more of the group of gases consisting of:

hydrogen; oxygen; nitrogen; hydrogen-oxygen mixtures; hydrogen-oxygen-inert gas mixtures; oxygen-nitrogen mixtures; oxygen-nitrogen-inert gas mixtures; nitrogen-hydrogen mixtures; nitrogen-hydrogen-inert gas mixtures; oxygen-nitrogen-hydrogen mixtures; oxygen-nitrogen-hydrogen-inert gas mixtures; oxygen-helium mixtures; nitrogen-helium mixtures; hydrogen-helium mixtures; oxygen-organohalogen mixtures; oxygen-organohalogen-inert gas mixtures; oxygen-organohalogen-nitrogen mixtures; oxygen-inorganic halogen mixtures; oxygen-inorganic halogen-inert gas mixtures; oxygen-inorganic halogen-nitrogen mixtures; oxygen-inorganic oxyhalogenated compound mixtures; oxygen-inorganic oxyhalogenated compound-inert gas mixtures; oxygen-inorganic oxyhalogenated compound-nitrogen mixtures.

11. A process in accordance with either of claims 1, 2 or 3 wherein said gaseous atmosphere is a mixture of oxygen and 8% $CF_4$ by volume.

12. A process in accordance with either of claims 1, 2 or 3 wherein said gas atmosphere is a mixture of 59.85% He, 39.9% $O_2$ and 0.25% $CF_4$ by volume.

13. A process in accordance with either of claims 1, 2 or 3 wherein said gas atmospher is a mixture of 60% $O_2$, 40% He by volume.

14. A process in accordance with either of the claims 1, 2 or 3 wherein gas is flowed through said chamber at a flow rate between 20 and 1000 scc/minute, corresponding to a total reaction pressure of 10 to 1000 microns of Hg, wherein the RF power density in the discharge lies between 0.0125 watts/cm$^3$ and 0.05 Watts/cm$^3$ and, wherein said materials and device are exposed to said gas plasma for a period from 5 to 90 minutes.

15. A method in accordance with either of claims 1, 2 or 3 wherein said gas is substantially pure nitrogen.

16. A method in accordance with either of claims 1, 2 or 3 wherein said gas is a mixture of nitrogen and oxygen.

17. A method for sterilization of medical devices and materials comprising the steps of, placing said devices and materials on a metallic electrode, said electrode being positioned within a gas-tight confining chamber, said chamber being made of metal and connected to a point of potential reference, the internal surface area of said chamber being substantially larger than the surface area of said electrode, evacuating said chamber to a substantially low pressure and introducing a gas into said chamber, initiating an electrical discharge in said gas within said chamber by application of RF voltage between said metallic electrode and the metal chamber wall creating a gas plasma, further including a perforated metallic enclosure within said chamber, and electrically insulated from it, said enclosure also being insulated from, and surrounding and containing, said metallic electrode and said devices and materials positioned thereon, whereby said devices and materials are contacted by substantially electrically neutral active species at a temperature below that which would be detrimental to said devices and materials, applying an RF voltage of one frequency to said perforated metallic enclosure and a different frequency to said metallic electrode, maintaining said gas plasma for a controlled period of time, maintaining a flow of said gas through said chamber while maintaining a pressure within the range of 10 microns Hg to 10 torr during said electrical discharge; and evacuating the gas plasma residual gases from said chamber prior to withdrawing said devices and materials from it.

18. A method for sterilization of medical devices and materials comprising the steps of, placing said devices and materials on a metallic electrode, said electrode being positioned within a gas-tight confining chamber, said chamber being made of metal and connected to a point of potential reference, the internal surface area of said chamber being substantially larger than the surface area of said electrode, evacuating said chamber to a substantially low pressure and introducing a gas into said chamber, initiating an electrical discharge in said gas within said chamber by application of RF voltage between said metallic electrode and the metal chamber wall creating a gas plasma, further including a perforated metallic enclosure within said chamber, said enclosure being insulated from, but surrounding and containing said metallic electrode and said devices and materials positioned thereon, said enclosure being connected to said point of potential reference, whereby said devices and materials are contacted by substantially electrically neutral active species at a temperature below that which would be detrimental to said devices and materials, maintaining said gas plasma for a controlled period of time, maintaining a flow of said through said chamber while maintaining a pressure within the range of 10 microns Hg to 10 torr during said electrical discharge; and evacuating the gas plasma residual gases from said chamber prior to withdrawing said devices and materials from it.

19. A method in accordance with any one of the claims 17 or 18, wherein said medical devices and materials are enclosed within pouches of gas permeable material when said devices and materials are placed within said chamber and remain so until said devices and materials are withdrawn from said chamber.

* * * * *